United States Patent [19] [11] 4,164,074

Lawler, deceased et al. [45] Aug. 14, 1979

[54] DENTAL ARTICULATOR WITH INTERCHANGEABLE MOUNTS

[75] Inventors: John K. Lawler, deceased, late of Gardena, Calif.; John W. Mitchell, Sr., Gardena; Kenneth H. Oyama, Huntington Beach, both of Calif.

[73] Assignee: Doris Gene Lawler, interest of John K. Lawler (deceased) passed as community property

[21] Appl. No.: 739,360

[22] Filed: Nov. 5, 1976

[51] Int. Cl.$^2$ ............................................. A61C 11/00
[52] U.S. Cl. ........................................................ 32/32
[58] Field of Search ............................................ 32/32

[56] References Cited

U.S. PATENT DOCUMENTS

| | | | |
|---|---|---|---|
| 1,814,750 | 7/1931 | Fritzenwallner | 32/32 |
| 2,608,762 | 9/1952 | Fox | 32/32 |
| 2,946,124 | 7/1960 | Coble | 32/32 |
| 3,067,515 | 12/1962 | Wilkinson | 32/32 |
| 3,123,914 | 3/1964 | Pietro | 32/32 |
| 3,359,639 | 12/1967 | Guichet | 32/32 |
| 3,510,947 | 5/1970 | Tuccillo et al. | 32/32 |
| 3,885,311 | 5/1975 | Lawler et al. | 32/32 |
| 4,030,197 | 6/1977 | Linck et al. | 32/32 |

FOREIGN PATENT DOCUMENTS 2053294  5/1972  Fed. Rep. of Germany ............ 32/32

Primary Examiner—Louis G. Mancene
Assistant Examiner—John J. Wilson
Attorney, Agent, or Firm—Howard L. Johnson

[57] ABSTRACT

Dental articulator formed with individually adjustable, upper and lower carrier plates, each having means for quick-coupling to one of an interchangeable pair of planar mounts (each mount adapted to adhesively support an assembled denture against one of its faces). A pair of matching dentures can thus be assembled either within or away from the articulator, mounted and tested for occlusion therein, and subsequently reworked (as often as necessary) either within or when removed from the articulator. Essentially a pair of thrust-coupling or threaded attachment means on the carrier plate or on the mount, engage corresponding sockets of the opposite member. Formulation of the mount of inexpensive plastic enables discard after single use. Three ball support for lower carrier plate provides closed loop movement simulating human jaw; combination of transverse hinge and ball suspension of upper carrier plate enables both transverse tilting on longitudinal axis and arcuate swing or upper mount toward and away from lower mount, thus enabling reworking of either mounted denture without removal from articulator.

8 Claims, 17 Drawing Figures

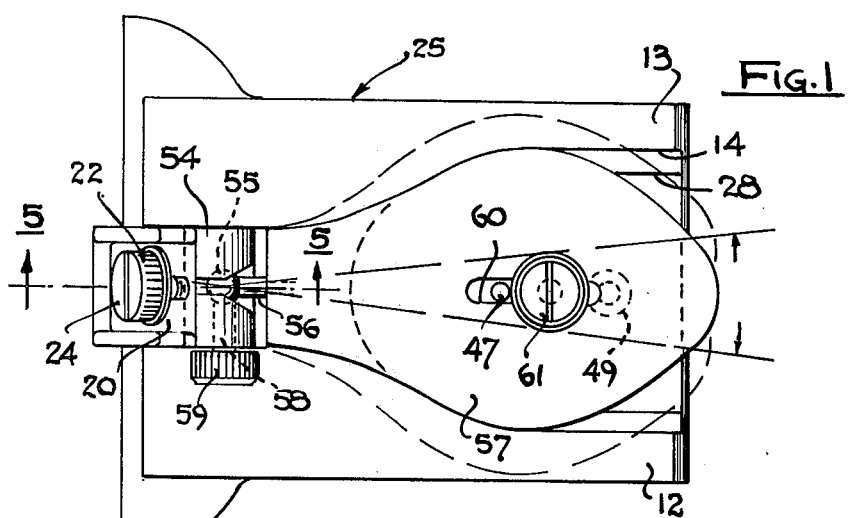
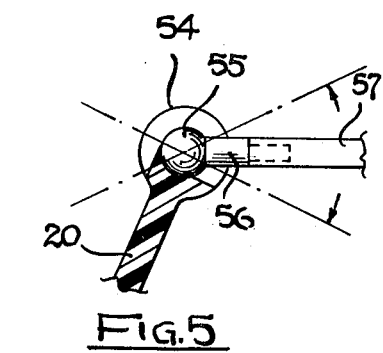
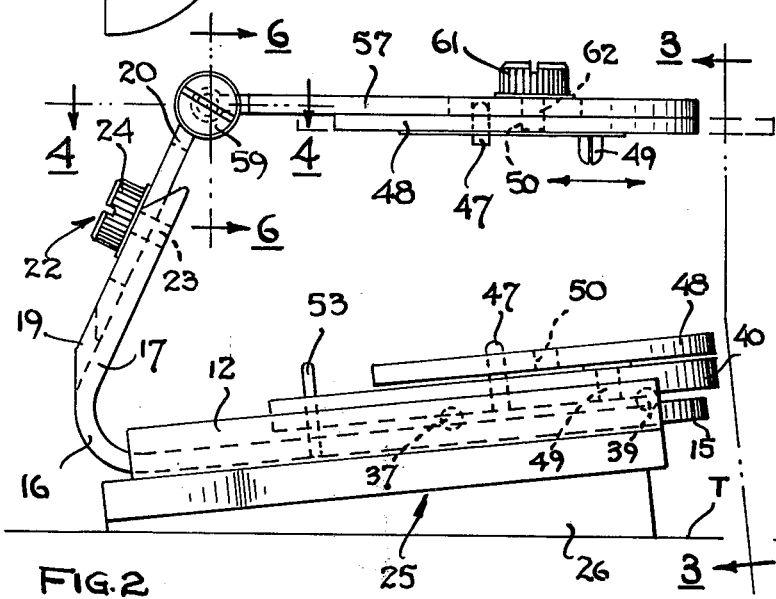
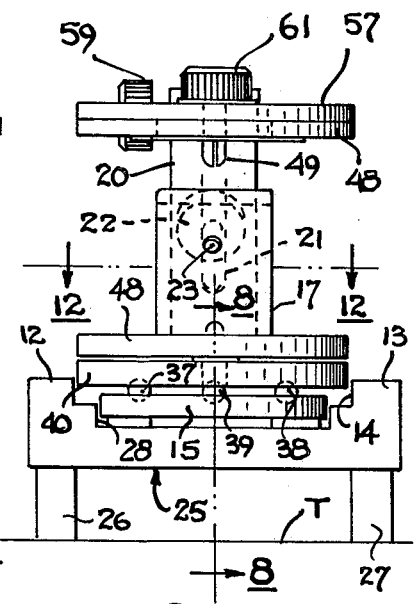
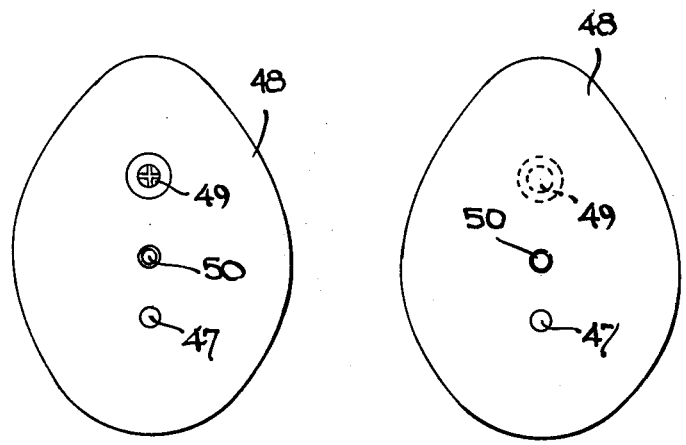
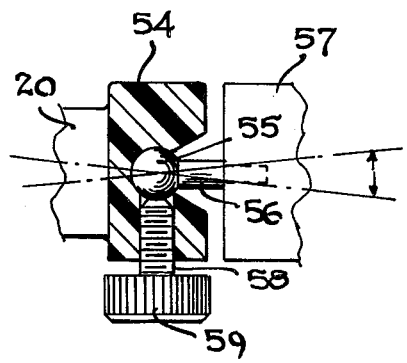

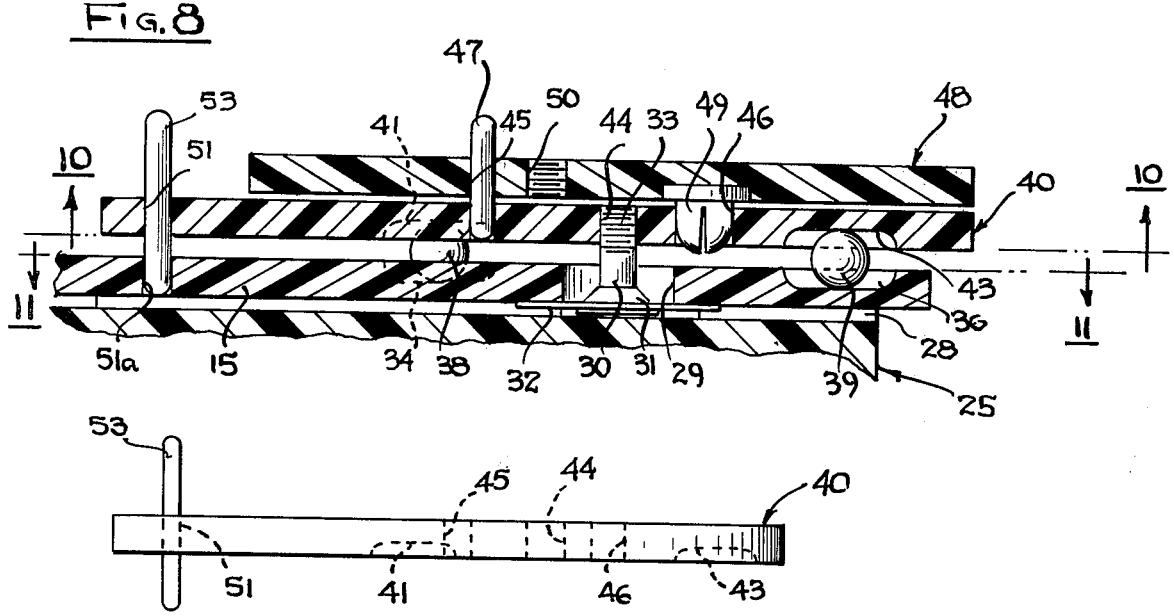
Fig. 8
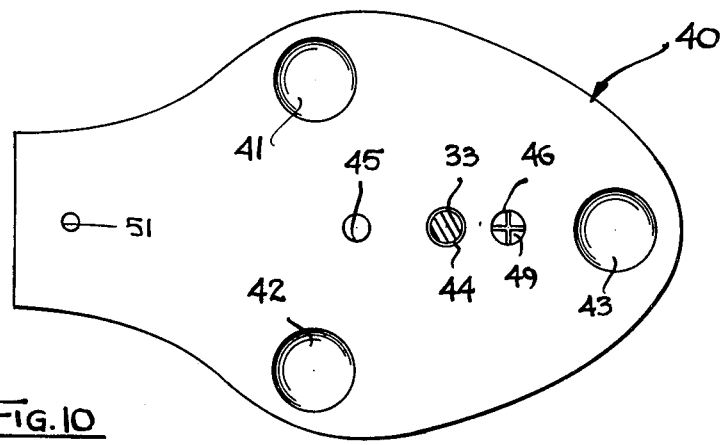
Fig. 9
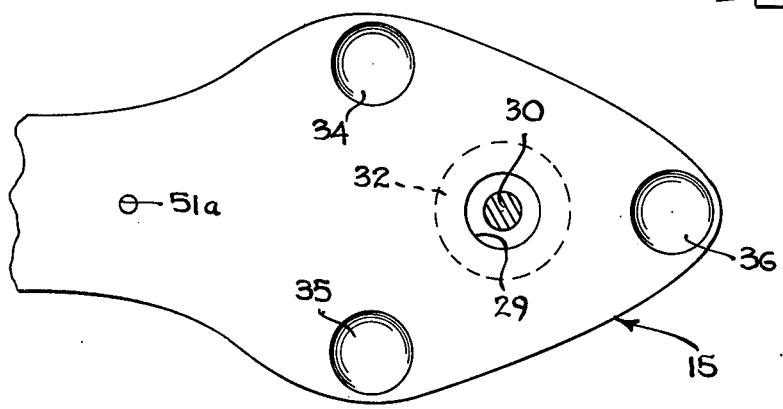
Fig. 10
Fig. 11
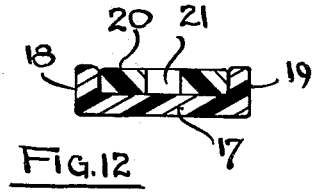
Fig. 12
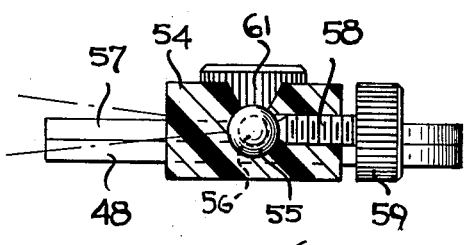
Fig. 6

DENTAL ARTICULATOR WITH INTERCHANGEABLE MOUNTS

BACKGROUND OF THE INVENTION

An ideal dental articulator should enable one denture carrying model (conforming to the inside of the human mouth) to be moved in the path of a closed loop, with transverse oscillation at any point of the circuit, corresponding generally to the movement of the lower jaw as dictated by the temporal-mandibular joint and its associated structures. To this should be added a minimal tilting movement of one denture relative to the other. Also, the pair of dentures when mounted in the articulator should be readily visible and workable from all three sides; and each denture or model should be removable for further work, at will, and be readily replaceable in the same position.

STATEMENT OF THE INVENTION

The present construction provides all of the above requirements in a notably economical and highly effective manner. In addition, there is provided a planar mount for each denture, which has thrust-engagement and/or threaded quick-coupling means by which it can be easily attached and detached, interchangeably in either the upper or lower carrier of the articulator. Such mount, fabricated for example of inexpensive, lightweight plastic material, can be discarded after a single usage in lieu of cleaning off the hardened plaster to prepare it for reuse. Easy thrust insertion of such mount in the articulator, enables the elements of a denture model,—arch, plate, plaster, wax, teeth, crowns, caps, bridges, etc.—to be put together on the mount while the latter is either in the articulator or outside, and to be moved in and out for testing and reconstruction at will. Either mount, that is, carrying either the upper or lower denture, can be placed on the lower carrier of the articulator and checked with the oval and transverse motion there provided (in conjunction with the other of the pair located in the upper carrier). If it turns out that the denture carried by the upper mount of the articulator requires more work, such as best performed by a downward-directed drill or instrument, the particular mount can be easily and quickly transferred to the lower carrier for such work.

A lower carrier support plate is carried by and supported above a base member by a trio of bearing balls, each of which is confined or retained within a shallow, flat-bottom cylindrical well so that each ball can roll anywhere within the recessed disk-shaped floor or bottom. Both the underface of the support plate and the upper face of the base is formed with such a trio of mutually facing recesses, each of a depth of less than the radius of the ball. The proximate ball, i.e. adjacent the open end of the articulator, and its pair of recesses, are located on the longitudinal axis of the lower denture; the two distal balls and recesses are located at respective corners of a triangle. In addition, the carrier and base plate are restrained against vertical separation while allowing the former limited juxtaposed movement relative to the latter, by provision of an upended, flange headed attachment post terminally anchored in the carrier plate and with its shaft laterally displaceable in an oversize bore of the base plate. In addition, the carrier can pivot horizontally when held atop any one of the trio of balls.

Such closed loop movement of the lower denture was possible by the construction of U.S. Pat. No. 3,885,311, although using a more complicated structure. However the present construction adds to this result, a construction by which the vertically adjustable, overhanging carrier plate (together with its mount) is both swingable on a horizontal hinge or axis toward and away from the base plate and its denture/mount, and also (by use of a ball joint) the upper carrier and denture/mount are tiltable transversely to its longitudinal axis. Such manipulation is important in enabling the technician to "wobble" the upper denture when in registration with the lower one, and from time to time to raise it up and tilt it from one side to the other for inspection or further grinding. Such result is obtained by either of two present constructions. In addition, with one form the upper carrier plate and overhanging member together with the upright support arm can be separated from the base plate and carrier, simply by removing the pivot pin, and the upper sub-unit then inverted and placed on a table for further work on its denture if desired.

There is also provided a support cradle for the whole assembly, having a rearward declining slide channel in which the base plate and lower carrier plate may be lodged so that the guide walls of the channel abut the respective edges of the plate and carrier and prevent lateral movement of the latter across the base. At the same time, provision of a vertical lock pin prevents longitudinal movement of the carrier. Such anchorage holds the mount and its denture against the noted closed loop movement when it is desired to work on the denture.

BRIEF DESCRIPTION OF THE DRAWINGS

FIG. 1 is a top plan view of our dental articulator shown held within the channel of a support cradle, the possible lateral movement of the upper carrier plate and mount (when not held by the lock) being indicated in broken lines.

FIG. 2 is a side elevational view thereof.

FIG 3. is an end elevational view taken from the right of FIG. 2.

FIG. 4 is a horizontal sectional view of a construction detail taken along the line 4—4 of FIG. 2.

FIG. 5 is a vertical longitudinal sectional view taken along the line 5—5 of FIG. 1, with parts in elevation.

FIG. 6 is a transverse sectional view taken along the line 6—6 of FIG. 2.

FIG. 7A is a bottom view of an interchangeable mount and FIG. 7B a top plan view, each of which faces adhesively supports a denture when such a pair of mounts is attached as shown in FIG. 2.

FIG. 8 is a longitudinal vertical sectional view of the lower structure taken along the line 8—8 of FIG. 3.

FIG. 9 is a side elevational view of the lower carrier plate, reduced from its size in FIG. 8.

FIG. 10 is a bottom plan view of the carrier plate of FIG. 9 with the anchorage post seen in section along the line 10—10 of FIG. 8.

FIG. 11 is a top plan view of the base plate, with the anchorage post seen in section along the line 11—11 of FIG. 8.

FIG. 12 is a transverse sectional view taken through the support bar along the line 12—12 of FIG. 3.

DETAILED DESCRIPTION OF PREFERRED EMBODIMENTS

Figure 13:
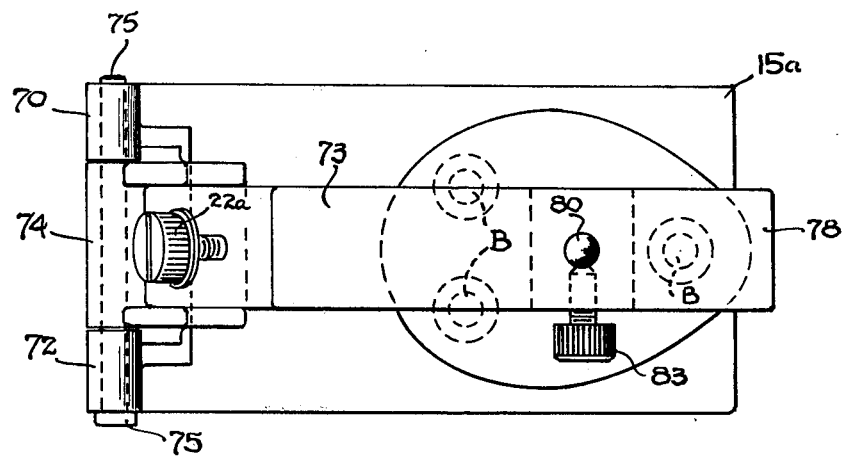
FIG. 13 is a top plan view of a modified articulator construction wherein the transverse hinge axis for the overhanging arm is located at the base level and the ball joint is on the carrier plate.

The illustrated embodiment of FIGS. 1–12 provides an articulator assembly employing a generally oval base plate 15, with generally planar and parallel upper and lower faces, at the further end laterally converging to form a flat tongue 16 which distally is angularly upturned to form a slanted support bar 17. A length of the outer face of the bar forms a positioning channel by reason of parallel edge beads or shoulders 18, 19 (FIG. 12). Partially lengthwise movable within the upstanded channel is a flat-faced support bar 20 which is formed with a midline slit aperture 21. A terminally threaded, anchorage post or screw 22 traverses the slit 21 with its inner end 23 threadedly engaging a tapped bore of the fixed bar 17, and a knurled and flanged head 24 overlying the outer face of the slidable bar 20 so as to anchor the latter at a selected position when tightened thereagainst.

The articulator as a unit and the base plate 15 in particular may be positioned or spaced above a suitable worksurface or table T by means of a longitudinal support frame or cradle 25 which is rearwardly downslanted by reason of a dependent pair of wedge-shaped support rails 26, 27. The upper surface of the cradle forms a downslanted slide-channel 28 of a width adapted to loosely engage the side edges of the base plate 15. Upstanding from the side edges of the channel are outwardly stepped, side walls 12, 13, which thus form a wider channel or guide/contact walls 14 above the slide channel 28.

The upper planar face of the base 15 is formed with three similar, shallow cylindrical or flat-bottom cavities 34, 35, 36 (FIG. 11), each of which loosely retains a ball bearing 37, 38, 39. Spacedly located or stacked above the base plate 15 is a carrier or slide plate 40, the underface of which is formed with a trio of downward-opening cylindrical cavities 41, 42, 43 (FIG. 10) of size and location similar to those in the base plate, so that in effect the slide plate 40 slides or is supported atop the three balls.

The base plate 15 is formed with a cylindrical, vertical aperture 29 which is traversed by a smaller diameter, smooth length 30 of an upthrust anchorage post or screw 31 which is characterized by a dependent head carrying an axial disk or flange 32 of greater periphery than the aperture 29 which it spanningly overlies. The margin of the flange thus always straddles the aperture 29 and permits the shaft portion 30 to be moved laterally within the oversize bore 29, that is, by movement of the overlying carrier 40 which is held by a threaded end 33 of the post 31 received in a threaded bore 44. When the base plate 15 is located in the channel 28 of the support frame 25, the edges of the carrier plate 40 will be restrained against lateral movement (across or with the trio of balls 37, 38, 39) by the side walls of the upper channel 14 as seen in FIG. 3. In addition, the distal end of the carrier is traversed by a smooth bore 51 through which an anchor pin 53 may be removably inserted into a socket 51a of the base plate in alignment therebeneath. The upper face of the carrier 40 has two thrust sockets or bores 45 and 46, the former to receive a thrust-coupling pin 47 and the latter a resilient, thrust-type grip fastener 49 of a detachable denture mount 48. Such a mount 48 supporting an upper or lower denture has the pin 47 fixedly extending from each face thereof, with additionally the grip-fastener 49 projecting from one face and the opposite face provided with a threaded socket 50. The presence of a pair of attachment points on each face of the mount prevents the coupled mount from pivoting about a single attachment point. That is, it is held firmly by the carrier plate 40; the latter can also be anchored relative to the base plate 15 jointly by the removable pin 53 and the upper channel walls 13, 14. However, with the articulator removed from the cradle 25 and the pin 53 withdrawn, the carrier 40 together with its mount and denture can be moved in a closed loop within the limitations permitted by the three balls and the movable post 31. Such temporary anchorage of the carrier 40 (by its location in the cradle) is particularly desirable when the denture is being assembled on the mount 48 which is atop the carrier.

The upper end of the slidable support bar 20 carries a transverse housing 54 (FIGS. 4, 5, 6) for a ball joint 55 from which a projecting stem 56 disposes a generally planar, overhanging plate or member 57. The ball is retained in a selected setting (for the plate 57) by a headed set screw 59 having its threaded shaft 58 disposed in a tapped aperture of the housing 54 with its inner end thus disposed to frictionally abut the ball 55. Thus the suspended plate 57 can be positioned horizontally within the range shown by the arrows in FIG. 4, and vertically within the span of the arrows of FIG. 5. Outwardly from the ball joint, the widening plate 57 is formed with a medial slot 60 which will loosely receive the upthrust end of a pin 47 (FIG. 1) of a mount 48 when the latter is held by the shaft 62 of a lock screw 61 which traverses the slot 60 with its end received in the socket 50. The mount 48 is thus positionable along the underface of the plate 57 within the range determined by shift of the pin 47 and shaft 62 lengthwise along the guide slot 60 (as indicated in broken lines in FIG. 2).

Figure 14:
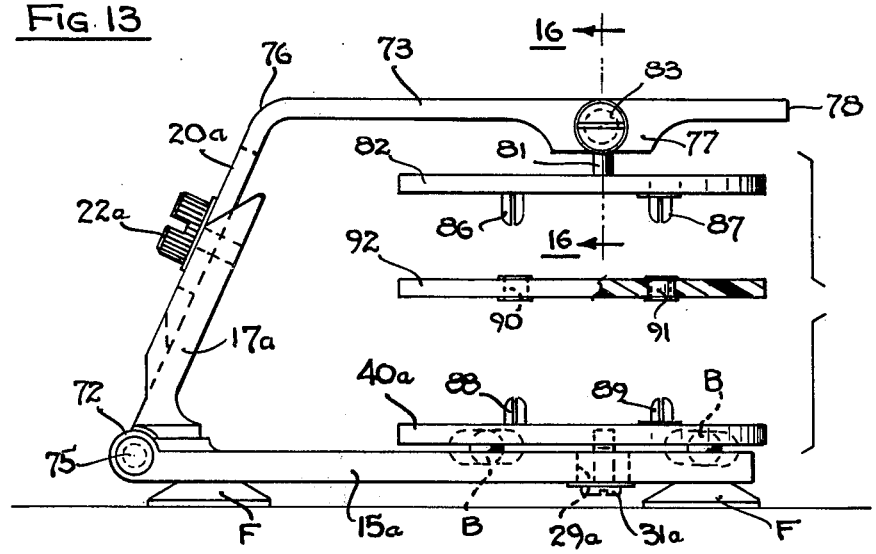
FIG. 14 is a side elevational view thereof, with detached mount.
Figure 15:
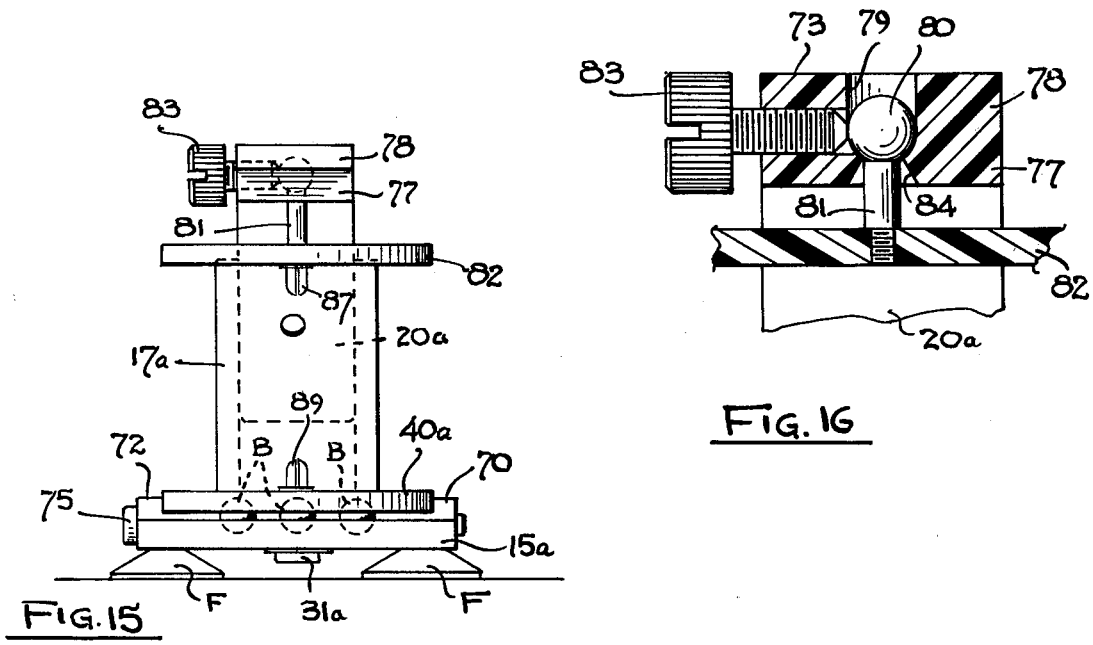
FIG. 15 is an end elevational view from the right of FIG. 14.
Figure 16:
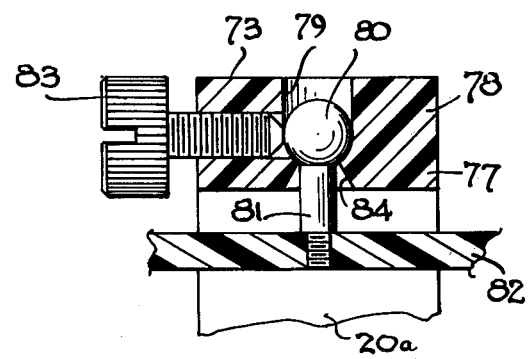
FIG. 16 is a transverse vertical section on line 16—16 of FIG. 14.

The modified construction of FIGS. 13–16 provides a lower carrier plate 40a and a base plate 15a separated by a trio of opposing-recess-held roller balls B, the plates held together by an inverted, disk-headed coupling post 31a terminally anchored to the carrier plate after traversing an oversize bore 29a of the base plate. The latter is dependently supported by short, flared pods or feet F which may be suction cups for better anchorage to a work bench or table. The base plate is rectangular shaped with a distal, bifurcate end formed with a pair of trunnions or bearing tubes 70, 72. An upstanding support bar 17a has its lower end formed as a bearing tube 74 of a length and proportion to fit between the pair of trunnions and thus receive a horizontal pivot pin 75 jointly therethrough. As in the prior form, the support bar is formed with a slide channel ascending along its distal face and adapted to receive a longitudinally slotted slide bar 20a which may be fastened at a selected height by an anchorage screw 22a.

The slide bar is obtusely crooked at 76 to form an overhanging panel or plate 78 having approximately the width of the upstanding length, and is thus disposed substantially horizontal and parallel to the base plate 15a and lower carrier plate 40a above which it is spaced. Intermediate its length, the plate is dependently thickened at 77 and vertically apertured at 79 (FIG. 16) to seat a ball joint 80 having a stem 81 dependently projecting from a conic counterbore 84 and terminally anchored in an upper carrier plate 82. A set screw 83 threadedly traverses the thickened housing portion 77 with its inner end bearing against the ball so as to hold it at a desired position when tightened. By such mounting of the carrier plate 82, the plate (and its carried denture) can be slanted by tilting the stem toward a wall of the conic socket 84 so as to bring the denture to an outswung position for inspection or grinding. In addition, the entire upper sub-assembly including the support bar 17a and connected slide bar 20a, overhanging plate 78 and carrier plate 82 can be separated as a unit from the base plate 15a simply by withdrawing the pivot pin 75; the unit can then be inverted and supported upon the upper face 73.

Both the upper 83 and lower 40a carrier plates carry a laterally spaced pair of resilient, thrust-engagement couplings 86, 87, 88, 89, disposed approximately in vertical alignment and adapted to be inserted into—from either face—a corresponding pair of apertures or grommets 90, 91 of a planar mount 92. Thus a pair of such mounts will attach their respective adhered dentures to the corresponding upper or lower carrier plate. Either mount can be held by either carrier plate. And with a denture model secured to one face, the opposite face of the mount can be attached initially to either carrier plate, and then, if desired, removed and after invertion, attached to the other carrier plate.

When the assembled dental elements fixed to a mount 48 are referred to collectively as a denture model or simply a denture, it will be appreciated that this is not limited to a complete upper or lower denture, but may be formed by inserting in the model partial replacement elements such as a bridge, crown, inley, arch, etc. of one jaw which it is then desired to match against the particular formation of the patient's other jaw. The opposing denture model may be fabricated from impressions in the known manner. Restoration of one or more teeth may of course be for one or both jaws.

Examples of synthetic resin or plastic from which the mounts may be molded include polycarbamate, acrylic, polyethylene, and polyphenylene sulfide.

The invention claimed is:

1. A dental articulator having a base member and an overhanging member disposed generally parallel to each other and adjustably spaced apart vertically, each member having attachment means adapted to hold one of a pair of dentures between them in position to effect simulated functional engagement of the pair, at least one of such members having associated means for laterally moving its denture relative to the other denture to test the occlusion of the pair, said attachment means comprising a pair of generally similar, planar and interchangeable mounts, each adapted to have an upper or lower denture transiently attached adjacent one face thereof, an opposite face of each mount having coupling means for its selective juxtaposition with its respective member, whereby a complementary pair of dentures may be thus disposed in mutual engagement and their occlusion tested by movement of one member and its coupled mount relative to the opposed member and coupled mount, and a support frame having a longitudinal slideway upon which said base member may be slidably supported for selective retention between lateral guide means disposed along opposite sides of the slideway in position to abut adjacent edges of a mount coupled to the base member; thereby restraining such mount from lateral displacement.

2. A dental articulator according to claim 1 wherein an upstanding connection member separates such base member and overhanging member, and the overhanging member is secured to the upstanding member by ball joint suspension means whereby the overhanging member may be selectively swung toward and away from the base member about a generally horizontal transverse axis, and also tilted transversely on a longitudinal axis extending therefrom.

3. A dental articulator according to claim 1 wherein said coupling means include a transverse-insertion element for each mount and associated means for adjustably positioning a mount lengthwise when coupled to said overhanging member.

4. A dental articulator according to claim 3 wherein the coupling means of each mount include a resilient thrust engagement element disposed adjacent one face of the mount, and screw thread engagement means disposed adjacent the opposite face of the mount.

5. A denture mount comprising a thin, generally planar body having an opposing pair of generally parallel faces, either one of which is adapted to transiently support a denture adhesively disposed in juxtaposition therewith for testing occlusion when such a pair of mounts are secured in an articulator, means on each of said pair, of parallel faces for cooperative engagement interchangeably with engagement means of an upper or lower support member of an articulator, said engagement means comprising at least two engagement elements laterally spaced apart along said opposite face, at least one of which elements comprises a socket for perpendicular seating of a cooperative projection element of an articulator.

6. A denture mount according to claim 5 wherein both of said engagement elements comprise thrust-engagement sockets.

7. A denture mount according to claim 5 wherein one of said engagement elements comprises a threaded socket.

8. A denture mount according to claim 5 wherein one of said engagement elements comprises a resilient thrust-engagement element projecting therefrom.

* * * * *